United States Patent [19]
Polito et al.

[11] 4,069,305
[45] Jan. 17, 1978

[54] I[125] IMIDAZOLE STEROID DERIVATIVES

[75] Inventors: Alan J. Polito, Costa Mesa; William S. Knight, Laguna Beach, both of Calif.

[73] Assignee: Beckman Instruments, Inc., Fullerton, Calif.

[21] Appl. No.: 684,688

[22] Filed: May 10, 1976

Related U.S. Application Data

[63] Continuation-in-part of Ser. No. 540,809, Jan. 14, 1975, Pat. No. 4,021,535.

[51] Int. Cl.² .................... A61K 43/00; C07J 17/00
[52] U.S. Cl. .................... 424/1; 260/239.5; 424/238
[58] Field of Search .............. 260/239.5; 424/1, 1.5, 424/12, 85, 238

[56] References Cited
PUBLICATIONS

Foster et al, Clinical Chemistry, vol. 20, No. 3, Mar., 1974, pp.365–368.
Farmer et al, Clinical Chemistry, vol. 20, No. 4, Apr., 1974, pp. 411–414.
McKenzie et al, J. of Clinical Endocrinology and Metabolism, vol. 38, No. 4, Apr., 1974, pp.622–627.
Newsome et al, Radioimmunoassay and Related Procedures in Medicine, vol. II, International Atomic Energy Agency, Vienna, 1974, pp. 79–85.

*Primary Examiner*—Benjamin R. Padgett
*Assistant Examiner*—Christine M. Nucker
*Attorney, Agent, or Firm*—Robert J. Steinmeyer; Robert S. Frieman

[57] ABSTRACT

Derivatives of steroids containing an imidazole group specifically bind to the desired antibody without non-specifically binding to other substances (e.g., proteins in a patient's plasma or serum and the surfaces of reaction vessels).

10 Claims, No Drawings

I[125] IMIDAZOLE STEROID DERIVATIVES

CROSS-REFERENCES TO RELATED APPLICATIONS

This application is a continuation-in-part of copending application, Ser. No. 540,809, filed January 14, 1975 now U.S. Pat. No. 4,021,535.

BACKGROUND OF THE INVENTION

1. Field of the Invention

This invention pertains to steroid derivatives containing an imidazole group wherein said derivatives are radioactively labeled. Said radioactively labeled derivatized steroids are useful in radioimmunoassay methods for assaying analogous, nonlabeled, underivatized steroids.

2. Description of the Prior Art

The use of $^{125}$I-tracers in steroid immunoassays has certain advantages in comparison with tritiated tracers. Besides the obvious advantage of the higher specific activity of the radioiodine over tritium, these $^{125}$I-tracers also result in a simpler and less expensive counting system (gamma counting as opposed to liquid scintillation counting). To produce $^{125}$I-labeles useful for steroid radioimmunoassay (RIA) techniques, two main approaches have been used. One approach entails the use of tyrosyl methyl ester (TME) derivatives of steroids which can be readily iodinated. U. Barbieri, A. Massaglia, M. Zannino, and U. Rosa, *J. of Chromat.*, 69:151 (1972) and A. R. Midgley, G. D. Niswender, V. L. Gay, and L. E. Reichert, *Recent Progr. Hormone*, 27:325 (1971). A second method entails iodinating steroid-protein constituents that have been used to raise antisera and using said iodinated steroid-protein conjugates as tracers. A. R. Midgley et al., supra, and S. L. Jeffcoate, E. D. Gilby, and R. Edwards, *Clinica Chemica Acta*, 42:343 (1973). A Massaglia, U. Barbieri, and C. SiriUpathum, *International J. of Applied Radiation and Isotopes*, 24:455 (1973), reported on the synthesis, purification, and iodination of cortisol-21-hemisuccinyl TME and cortisol-3-(O-carboxymethyl) oxime-TME derivatives. In the same year, R. Mavano, C. Dotti, and P. Grosso, *Clinica Chemica Acta*, 47:167 (1973), reported on the employment of $^{125}$I-labeled cortisol-21-hemisuccinyl-TME as a tracer in the competitive protein binding assay using transcortin as the binder. Since iodination of an estradiol TME derivative results in iodine substitution of the A ring and consequently a loss of the immunoreactivity of the tracer (P. W. Nars and W. M. Hunter, *J. Endocr.*, 57:XLVII (1973) and E. D. Gilby, S. L. Jeffcoate, and R. Edwards, *J. Endocr.*, 58:XX (1973)), histamine was first iodinated and subsequently coupled to an estradiol-6-(O-carboxymethyl) oxime hapten using a mixed anhydride synthesis. B. F. Erlinger, F. Borek, F. M. Beiser, and S. Lieberman, *J. Biol. Chem.*, 228:713 (1957). The same mixed anhydride synthesis procedure has also been used to prepare estradiol-6-(O-carboxymethyl) oxime-$^{125}$I-tyramine (P. Linberg and L. E. Edquist, *Clinica Chemica Acta*, 53:169 (1974)) and progesterone-3-(O-carboxymethyl) oxime $^{125}$I-histamine (J. J. Scarisbrick and E. H. D. Cameron, *J. of Steroid Biochem.*, 6:51 (1975)) tracers for use in RIA.

It has been discovered that unlike tyrosine derivatives which yield a tracer possessing a lower affinity for the antisera than the unlabeled steroid and also giving a high nonspecific background count in polystyrene and polypropylene vials, particularly in the presence of naturally occurring serum constituents histamine derivatives of steroids alleviate these problems and therefore yield labeled haptens which are much superior for use in RIA.

SUMMARY OF THE INVENTION

Radioimmunoassay reagents having a structural formula I

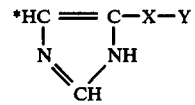

Formula I wherein the asterisk (*) indicates radioactive labeling, wherein X is any suitable bridge, and wherein Y is a steroid, are excellent radioimmunoassay reagents for use in radioimmunoassay procedures because said reagents specifically bind to the desired antibodies without nonspecifically binding to other substances (e.g., proteins in a patient's plasma or serum and the surfaces of reaction vessels).

DESCRIPTION OF THE PREFERRED EMBODIMENTS

The radioimmunoassay reagents within the scope of this invention have structural formula I, supra, wherein asterisk (*) indicates radioactive labeling, wherein X is any suitable bridge, and wherein Y is a steroid. Exemplary radioactive labels include I[125] and I[131]. Preferably, the radioimmunoassay reagents of this invention are radioactively labeled with [125]I.

Exemplary bridges which may be used in the radioimmunoassay reagents of this invention include (O-carboxymethyl) hydroxylamine (B. F. Erlanger, F. Dorek, S. M. Beiser, and S. Lieberman, *J. Biol. Chem.*, 228:713 (1957)), succinic anhydride (G. E. Abraham, P. K. Grover, W. D. Odell, and W. Daughaday, Principles of Competitive Protein Binding Assays, J. P. Lippincott, Philadelphia, Penna., pg. 140, (1971)), and thioether bridges (A. Weinstein, H. R. Lindner, A. Friedlander, and S. Bauminger, *Steroids*, 20(6):789 (1972)). When one wishes to connect histamine via a bridge to the three position of the steroid ring wherein said three position has attached thereto a keto group, the preferred bridge is an (O-carboxymethyl) oxime bridge.

Y can be any steroid. The steroids of choice for use in this invention are cortisol and aldosterone.

Steroid derivatives made with histamine do not nonspecifically bind to other substances (e.g., proteins in a patient's plasma or serum and the surfaces of reaction vessels) while specifically binding to the desired antibodies.

Copending application Ser. No. 540,809 notes that "[i]t is thought that the reduction in nonspecific binding with [an imidazoleacetic acid derivative] as compared to corresponding digoxin derivative of p-hydroxyphenylpropionic acid is due to the polar nature of the imidazole group relative to the non-polar characteristics of he phenyl group." Therefore, in view of this theory it is clear that the characteristics of the steroid linked to the imidazole group containing moiety (e.g., imidazoleacetic acid, histamine, etc.) via any suitable bridge is immaterial in that the low blanks and low interference with albumin of said imidazole group containing steroid derivatives are due solely to presence of said imidazole group.

The radioimmunoassay reagents within the scope of this invention can be prepared by techniques well known to those skilled in the art. See G. E. Abraham, *Acta Endocrinologica*, Suppl. 183, pp. 11 to 14, (1974), said publication being incorporated herein in toto by reference.

The radioimmunoassay procedure within the scope of this invention entails the use of any radioimmunoassay procedure known to those skilled in the art wherein said procedure employs the novel radioactively labeled imidazole group containing steroid derivatives of this invention. A general description of radioimmunoassay procedures can be found in C. S. Skelley, L. P. Brown and P. K. Besch, "Radioimmunoassay", *Clinical Chemistry*, Vol. 19, No. 2, 146–186 (1973), said publication being incorporated herein in toto by reference.

The following examples are provided for the purpose of further illustration only and are not intended to be limitations on the disclosed invention.

EXAMPLE 1

Preparation of Cortisol-3-Oxime:

Cortisol (41.54 mg), 21.17 mg of carboxymethoxylamine and 41.43 mg of sodium acetate were dissolved in 10.0 ml of dry methanol and the reaction was allowed to proceed overnight with stirring at room temperature. Two 20 × 20 cm preparative H. F. thin-layer plates (2 mm, E. Merk, Darmstadt, Germany) were each streaked with 420 ml of the reaction mixture and developed in a benzene/methanol (60:40) solution. The solvent system separated the cortisol-3-oxime ($R_F = 0.32$) from both the unreacted cortisol ($R_F = 0.78$) and a small amount of cortisol-3,20-dioxime. The ban containing the cortisol-3-oxime was scraped from the plate and extracted three times with 10 ml of methanol. The combined extracts were taken to dryness on a flash-evaporator and redissolved in 2 ml of methanol. After any remaining particulate material was removed by centrifugation, 30 μl of the clear solution was spotted on a 5 × 10 cm analytical HF-TLC plate (0.25 mm) and developed in the same solid system. A single band appeared which gave a positive test with tetrazolium blue reagent (J. K. McKenzie and J. A. Clements, *J. Clin. Endocrinol. Metab.*, 38:622 (1974)). This result is indicative of a C-20 keto group being present. Finally, a yield of 27.8 mg (67%) of cortisol-3-oxime was determined by ultraviolet spectroscopy.

EXAMPLE 2

Preparation of cortisol-3-oxime-histamine:

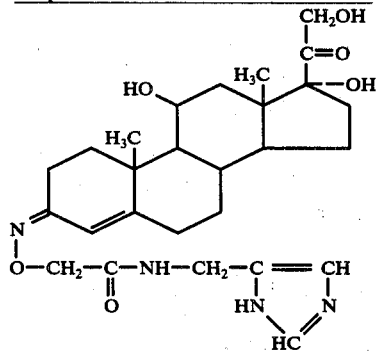

A methanolic solution (1.3 ml) containing 6.37 mg/ml of cortisol-3-oxime was taken to dryness under nitrogen in a 2 ml screw-capped reaction vessel. After the addition of 300 μl of dry dioxane, the vessel was cooled in a 10° C. ice-water bath for 10 to 15 minutes. Tributylamine (10 μl) was added to 50 μl of dry dioxane and, after mixing, 30 μl of the resulting solution was added to the cortisol-3-oxime solution with mixing. After this reaction mixture was cooled to 10° C., 30 μl of a solution containing 10 μl of isobutylchloroformate in 100 μl of dry dioxane was added. After the addition of the isobutylchloroformate, the reaction mixture was stirred for 20 to 25 minutes at 10° C.

During the above reaction period, 11 mg of histamine was dissolved in a mixture of 200 μl of dioxane, 200 μl of water, and 20 μl of a 0.5 N sodium hydroxide solution. This histamine solution was also cooled to 10° C. and, after the above 20 to 25 minute reaction period, added to the solution containing the isobutylformate mixed anhydride of cortisol-3-oxime. This step was allowed to proceed for 3 hours at 10° C. and then gradually the temperature was brought to room temperature by leaving the reaction vessel in an ice-water bath overnight.

The next day, the reaction mixture was streaked on two 20 × 20 cm analytical H.F.-TLC plates (0.25 ml) and the plates were developed in a chloroform/methanol/water (18:4:2) solution. This system separated both the unreacted histamine ($R_F = 0.33$) and cortisol-3-oxime ($R_F = 0.075$) from the cortisol-3-oxime histamine derivative ($R_F = 0.17$). Histamine and the histamine cortisol compound both could be visualized by a reaction with Pauley's reagent (see C. W. Easley, *Biochem. Biophys. Acta*, 107:386 (1965)), whereas unreacted cortisol and the histamine cortisol compound both were identified by reaction with the tetrazolium blue reagent. Ultraviolet spectroscopy of the purified cortisol-3-oxime histamine derivative in methanol gave a yield of 0.65 mg (7.8%).

EXAMPLE 3

Iodination procedure:

Cortidol-3-oxime histamine derivative (20 μl; 0.1 μgm/μl) in dry methanol, 50 μl of water, 20 μl of a 0.5M sodium phosphate buffer having a pH of 7.4, 10 μl of Na$^{125}$I (2 millicuries) and 20μl of chloramine-T (5 mgm/ml in a 0.5M phosphate buffer having a pH of 7.4) were mixed and allowed to react for two minutes at room temperature. The reaction was terminated by the addition of 20 μl of sodium metabisulfite (5 mg/ml in a 0.5M phosphate buffer having a pH of 7.4). The reaction mixture was spotted on a 5 × 20 cm analytical HF-TLC plate and developed in a chloroform:methanol:water (18:4:2) solution. The band containing the mono-$^{125}$I-labeled cortisol-3-oxime histamine derivative was located by radioautography ($R_F = 0.53$). The material was extracted into dry methanol (4 ml) and diluted into 76 ml of a 0.1% acetic acid/water solution. An average iodination produced about 800 microcuries of labeled hapten (40% yield).

Iodinated aldosterone-3-oxime histamine derivatives can be prepared via a procedure analogous to that set forth in examples 1 through 3.

EXAMPLE 4

Cortisol Assay Protocol:

1. Label twenty (20) tubes in duplicate as follows: T.C., blank, $B_o$, A through F, and CS (control serum). Label two (2) tubes, in duplicate, for each patient serum sample.
2. Add 200 μl sterile distilled water to blank tubes.
3. Add 20 μl of buffer to the $B_o$ tubes.
4. Add 20 μl of standards A through F to the appropriate tubes.
5. Add 20 μl of controlserum to CS tubes.
6. Add 20 μl of each patient's serum to the appropriate tubes.
7. Add 400 μl of the $^{125}$I-cortisol-precipitating antibody mixture to all tubes. Immediately before use, vortex mix the mixture for five (5) to ten (10) seconds. Cap T.C. tubes and set aside.
8. Add 200 μl of dilute cortisol antiserum to all tubes except T.C. and blank. Cap all tubes and mix by gentle swirling or gentle vortexing.
9. Incubate for two (2) hours at 37° C. (except T.C. tubes).
10. Add 1 ml cold (2° C. to 8° C.) saline to each tube (except T.C.) and cap tubes.
11. Immediately centrifuge all tubes (except T.C.) for fifteen (15) minutes at a minimum of 1500 × g.
12. Carefully decant each tube (except T.C.) and discard supernatant. After decanting, gently blot the remaining supernatant which rims the top of the tube against plastic-backed absorbent paper. Cap all tubes.
13. Count all tubes, including T.C., for a length of time to give reasonable counting statistics for each tube (e.g., 10,000 counts gives 26 counting error of 2%). This should be between one (1) and ten (10) minutes.

This protocol is listed in tabular form in Table I.

1. Use the following formula to calculate the amount of labeled cortisol bound to anti-cortisol in the absence of any unlabeled cortisol.

$$\%B_o = \frac{B_o \text{ counts} - \text{blank}}{T.C. \text{ counts} - \text{blank}} \times 100$$

The $B_o$ should be between 40 and 60%.

2. Determine the amount of labeled cortisol bound to anticortisol in standard and patient sample vials as follows:

$$\%B = \frac{B \text{ counts for standard or patient sample} - \text{blank}}{T.C. \text{ counts} - \text{blank}} \times 100$$

3. Plot %B values of standards against μg/dl cortisol on two-cycle semilogarithmic graph paper with μg/dl cortisol on the log scale.
4. Determine the concentrations of cortisol in patient sample and control serum from the standard curve.

Data obtained by following the procedure of Example 4 is set forth in Table II. This data can be plotted, as discussed above, thereby enabling one to generate a standard curve.

TABLE II

| Standards or Control Sera | %B | Concentration μg/dl | Concentration Extrapolated From Standard Curve, μg/dl |
|---|---|---|---|
| $B_o$ | 52.0 | 0 | |
| $B_o$ | 54.8 | 0 | |
| A | 48.1 | 1.0 | |
| A | 49.3 | 1.0 | |
| B | 44.5 | 2.0 | |
| B | 44.3 | 2.0 | |
| C | 36.2 | 5.0 | |
| C | 36.1 | 5.0 | |
| D | 24.8 | 10.0 | |
| D | 26.2 | 10.0 | |
| E | 17.9 | 20.0 | |
| E | 18.1 | 20.0 | |
| F | 9.5 | 50.0 | |
| F | 9.3 | 50.0 | |
| Beckman CS | 17.0 | | 23.4 ± 0.1 |
| Beckman CS | 17.0 | | 23.5 ± 0.1 |
| Ortho I | 23.0 | | 13.2 ± 0.7 |

TABLE I

| Sample | Distilled Water (μl) | Buffer (μl) | Standard or Sample (μl) | $^{125}$I-Cortisol-Precipitating Antibody Mixture (μl) | Dilute Anti-Cortisol (μl) |
|---|---|---|---|---|---|
| T.C. | 0 | 0 | 0 | 400 | 0 |
| Blank | 200 | 0 | 0 | 400 | 0 |
| $B_o$ | 0 | 20 | 0 | 400 | 200 |
| A (1 μg/dl) | 0 | 0 | 20-A | 400 | 200 |
| B (2 μg/dl) | 0 | 0 | 20-B | 400 | 200 |
| C (5 μg/dl) | 0 | 0 | 20-C | 400 | 200 |
| D (10 μg/dl) | 0 | 0 | 20-D | 400 | 200 |
| E (20 μg/dl) | 0 | 0 | 20-E | 400 | 200 |
| F (50 μg/dl) | 0 | 0 | 20-F | 400 | 200 |
| Control Serum | 0 | 0 | 20-CS | 400 | 200 |
| Patient Sample 1 | 0 | 0 | 20-Sample | 400 | 200 |
| Patient Sample 2 etc. | 0 | 0 | 20-Sample | 400 | 200 |

An analogous protocol can be used in a RI procedure for aldosterene.

There are several methods used to plot standard curves and obtain the concentration of serum constituent. Methods used include: B/T or $B/B_o$ versus concentration or log concentration. T/B versus concentration, or logit $B/B_o$ versus log concentration. The plot of B/T versus log concentration method is as follows:

TABLE II-continued

| Standards or Control Sera | %B | Concentration μg/dl | Concentration Extrapolated From Standard Curve, μg/dl |
|---|---|---|---|
| Ortho I | 24.4 | | 11.9 ± 0.7 |

Table II also lists RIA results obtained using Beckman and Ortho I control sera.

As in the case of digoxin, the iodinated steroids derivatives of formula I, e.g., iodinated cortisol and aldosterone derivatives, containing an imidazole group alleviate various problems associated with prior art steroid derivatives, e.g., lower affinity for the antisera than the unlabeled steroid, high nonspecific background count in reaction vessels, etc.

Based on this disclosure, many other modifications and ramifications will naturally suggest themselves to those skilled in the art of immunoassay procedures. These are intended to be comprehended as within the scope of this invention.

The embodiments of the invention in which an exclusive property or privilege is claimed are defined as follows:

1. A radioimmunoassay reagent having a structural formula selected from a group consisting of

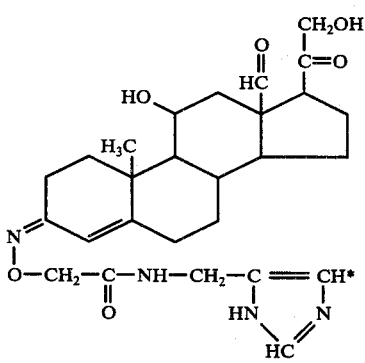

and

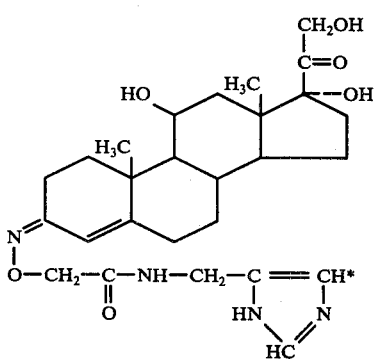

wherein the asterisk (*) indicates radioactive labelling.

2. The radioimmunoassay reagent of claim 1 having the structural formula

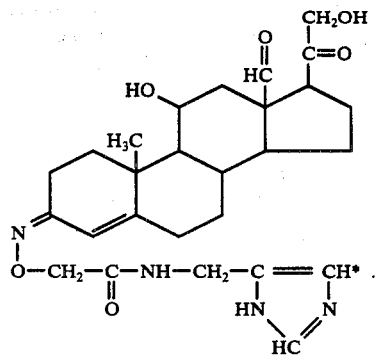

3. The radioimmunoassay reagent of claim 2 wherein the radioactive labelling is with $^{125}$I.

4. The radioimmunoassay reagent of claim 1 having the structural formula

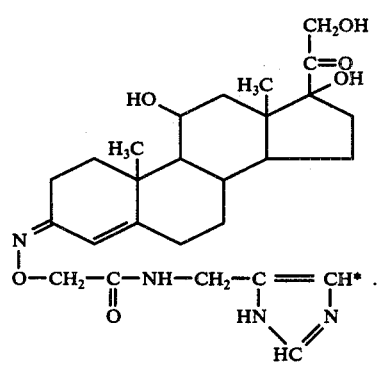

5. The radioimmunoassay reagent of claim 4 wherein the radioactive labelling is with $^{125}$I.

6. A radioimmunoassay method for assaying a steroid selected from a group consisting of cortisol and aldosterone, wherein the improvement comprises using in said method a radio-immunoassay reagent having a structural formula selected from a group consisting of

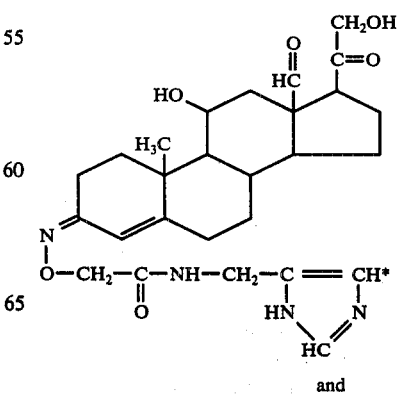

and

-continued

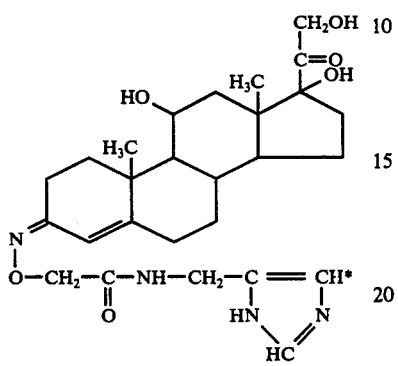

wherein the asterisk (*) indicates radioactive labelling.

7. The radioimmunoassay method of claim 6 for assaying cortisol, wherein the radioimmunoassay reagent has the structural formula

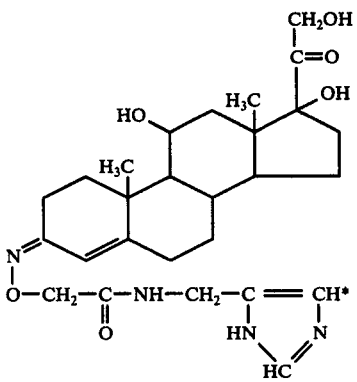

8. The radioimmunoassay method of claim 7 wherein the radioimmunoassay reagent is radioactively labeled with 125I.

9. The radioimmunoassay method of claim 6 for assaying aldosterone, wherein the radioimmunoassay reagent has the structural formula

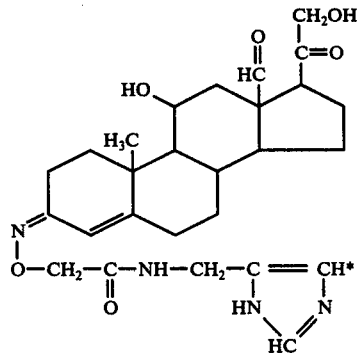

10. The radioimmunoassay method of claim 9 wherein the radioimmunoassay reagent is radioactively labeled with 125I.

* * * * *